United States Patent
Lawrence et al.

(10) Patent No.: US 8,904,859 B2
(45) Date of Patent: Dec. 9, 2014

(54) DETECTING GAS COMPOUNDS FOR DOWNHOLE FLUID ANALYSIS

(75) Inventors: Jimmy Lawrence, Amherst, MA (US);
Tim G. J. Jones, Cambridge (GB);
Kentaro Indo, Sugar Land, TX (US);
Tsutomu Yamate, Yokohama (JP);
Noriyuki Matsumoto, Yokohama (JP);
Michael M. Toribio, Toronto (CA);
Hidetoshi Yoshiuchi, Fujisawa (JP);
Andrew Meredith, Cambridge (GB);
Nathan S. Lawrence, Cambridgeshire (GB); Li Jiang, Katy, TX (US); Go Fujisawa, Sagamihara (JP); Oliver C. Mullins, Ridgefield, CT (US)

(73) Assignee: Schlumberger Technology Corporation, Sugar Land, TX (US)

(*) Notice: Subject to any disclaimer, the term of this patent is extended or adjusted under 35 U.S.C. 154(b) by 358 days.

(21) Appl. No.: 13/353,321

(22) Filed: Jan. 19, 2012

(65) Prior Publication Data

US 2012/0137764 A1  Jun. 7, 2012

Related U.S. Application Data (63) Continuation-in-part of application No. 12/198,129, filed on Aug. 26, 2008, now abandoned.

(51) Int. Cl.
*E21B 49/08* (2006.01)
*E21B 49/00* (2006.01)
*G01N 33/28* (2006.01)

(52) U.S. Cl.
CPC .......... *E21B 49/005* (2013.01); *G01N 33/2823* (2013.01); *E21B 49/08* (2013.01)
USPC .................................................... 73/152.28

(58) Field of Classification Search
USPC .................. 73/152.19, 152.23, 152.28
See application file for complete search history.

(56) References Cited

U.S. PATENT DOCUMENTS 5,066,398 A * 11/1991 Soria et al. ............... 210/321.89
5,121,627 A *  6/1992 D'Aoust .................... 73/19.05
(Continued)

FOREIGN PATENT DOCUMENTS

GB       2359631       8/2001
GB       2371621       7/2002
(Continued)

OTHER PUBLICATIONS

GB Examination Report dated Feb. 28, 2012 for corresponding GB application No. 1104992.1.
(Continued)

*Primary Examiner* — John Fitzgerald
(74) *Attorney, Agent, or Firm* — Daryl R. Wright; Jody DeStefanis (57) ABSTRACT

A gas separation and detection tool for performing in situ analysis of borehole fluid is described. The tool comprises a sampling chamber for a downhole fluid. The sample chamber comprises a detector cell with an opening. The tool also comprises a gas separation module for taking a gas from the downhole fluid. The gas separation module comprises a membrane located in the opening, a support for holding the membrane, and a sealant applied between the housing and the membrane or support. Moreover, the tool comprises a gas detector for sensing the gas.

18 Claims, 9 Drawing Sheets

(56) References Cited

U.S. PATENT DOCUMENTS

| | | | |
|---|---|---|---|
| 5,351,532 A * | 10/1994 | Hager | 73/152.55 |
| 6,223,822 B1 * | 5/2001 | Jones | 166/250.05 |
| 6,228,146 B1 * | 5/2001 | Kuespert | 95/46 |
| 6,272,938 B1 | 8/2001 | Singh et al. | |
| 6,466,513 B1 * | 10/2002 | Pabon et al. | 367/35 |
| 6,939,717 B2 | 9/2005 | Jiang et al. | |
| 6,953,493 B2 | 10/2005 | Nakayama et al. | |
| 6,995,360 B2 | 2/2006 | Jones et al. | |
| 7,059,179 B2 * | 6/2006 | Proett et al. | 73/152.05 |
| 7,062,958 B2 * | 6/2006 | Diakonov et al. | 73/152.23 |
| 7,100,689 B2 * | 9/2006 | Williams et al. | 166/264 |
| 7,231,819 B2 * | 6/2007 | Jones et al. | 73/152.23 |
| 7,240,546 B2 * | 7/2007 | DiFoggio | 73/152.23 |
| 7,318,343 B2 * | 1/2008 | Coenen | 73/152.19 |
| 7,395,704 B2 * | 7/2008 | DiFoggio | 73/152.42 |
| 7,464,588 B2 * | 12/2008 | Steinsiek | 73/152.55 |
| 7,500,388 B2 * | 3/2009 | Fujisawa et al. | 73/152.11 |
| 7,513,147 B2 * | 4/2009 | Yogeswaren | 73/152.58 |
| 7,516,654 B2 * | 4/2009 | DiFoggio | 73/152.23 |
| 7,520,160 B1 * | 4/2009 | Toribio et al. | 73/31.05 |
| 7,644,760 B2 * | 1/2010 | Woloson | 166/250.01 |
| 7,748,266 B2 | 7/2010 | Evrard et al. | |
| 7,814,782 B2 | 10/2010 | DiFoggio | |
| 2002/0014106 A1 * | 2/2002 | Srinivasan et al. | 73/23.42 |
| 2002/0121370 A1 | 9/2002 | Kurkjian et al. | |
| 2003/0134426 A1 | 7/2003 | Jiang et al. | |
| 2003/0206026 A1 | 11/2003 | Diakonov et al. | |
| 2004/0045350 A1 | 3/2004 | Jones et al. | |
| 2004/0159149 A1 * | 8/2004 | Williams et al. | 73/152.23 |
| 2004/0173094 A1 | 9/2004 | Nakayama et al. | |
| 2005/0000279 A1 * | 1/2005 | Yogeswaren | 73/152.58 |
| 2005/0109098 A1 * | 5/2005 | DiFoggio | 73/152.55 |
| 2005/0229779 A1 | 10/2005 | Nakayama et al. | |
| 2005/0241382 A1 | 11/2005 | Coenen | |
| 2005/0269499 A1 | 12/2005 | Jones et al. | |
| 2006/0008913 A1 | 1/2006 | Angelescu et al. | |
| 2006/0185430 A1 * | 8/2006 | Yogeswaren | 73/152.16 |
| 2009/0044617 A1 * | 2/2009 | DiFoggio | 73/152.55 |
| 2009/0090176 A1 * | 4/2009 | Toribio et al. | 73/152.18 |
| 2010/0050761 A1 * | 3/2010 | Lawrence et al. | 73/152.28 |
| 2010/0132434 A1 * | 6/2010 | Moake | 73/1.82 |
| 2010/0279173 A1 * | 11/2010 | Hying et al. | 429/247 |
| 2014/0212727 A1 * | 7/2014 | Hying et al. | 429/144 |

FOREIGN PATENT DOCUMENTS

| | | |
|---|---|---|
| GB | 2363809 | 9/2002 |
| GB | 2415047 | 12/2005 |
| GB | 2467659 | 8/2010 |
| WO | 2005/017514 | 2/2005 |
| WO | 2005/066618 | 7/2005 |
| WO | 2005/121779 | 12/2005 |

OTHER PUBLICATIONS

Examination report for the equivalent GB patent application No. 1104992.1 issued on Jul. 10, 2012.

* cited by examiner

DETECTING GAS COMPOUNDS FOR DOWNHOLE FLUID ANALYSIS

CROSS REFERENCE TO RELATED APPLICATION

This application is a continuation-in-part of U.S. patent application Ser. No. 12/198,129 filed Aug. 26, 2008 and entitled "DETECTING GAS COMPOUNDS FOR DOWNHOLE FLUID ANALYSIS," which is hereby incorporated in its entirety by this reference.

FIELD OF THE INVENTION

The invention is generally related to downhole fluid analysis, and more particularly to in situ detection of gaseous compounds in a borehole fluid.

BACKGROUND OF THE INVENTION

Phase behavior and chemical composition of borehole fluids are used to help estimate the viability of some hydrocarbon reservoirs. For example, the concentration of gaseous components such as carbon dioxide, hydrogen sulfide and methane in borehole fluids are indicators of the economic viability of a hydrocarbon reservoir. The concentrations of various different gasses may be of interest for different reasons. For example, $CO_2$ corrosion and $H_2S$ stress cracking are leading causes of mechanical failure of production equipment. $CH_4$ is of interest as an indicator of the calorific value of a gas well. It is therefore desireable to be able to perform fluid analysis quickly, accurately, reliably, and at low cost.

A variety of techniques and equipment are available for performing fluid analysis in a laboratory. However, retreiving samples for laboratory analysis are time consuming. Further, some characteristics of borehole fluids change when brought to the surface due to the difference in environmental conditions between a borehole and the surface and other factors. For example, because hydrogen sulfide gas readily forms non-volatile and insoluble metal sulfides by reaction with many metals and metal oxides, analysis of a fluid sample retrieved with a metallic container can result in an inaccurate estimate of sulfide content. This presents a technological problem because known fluid analysis techniques that can be used at the surface are impractical in the borehole environment due to size limitations, extreme temperature, extreme pressure, presence of water, and other factors. Another technological problem is isolation of gases, and particular species of gas, from the borehole fluid.

The technological problems associated with detection of gas in fluids have been studied in this and other fields of research. For example, US20040045350A1, US20030206026A1, US20020121370A1, GB2415047A, GB2363809A, GB2359631A, US6995360B2, US6939717B2, WO2005066618A1, WO2005017514A1, WO2005121779A1, US20050269499A1, and US20030134426A1 describe an electrochemical method for H2S detection using membrane separation. US20040045350A1, GB2415047A, and GB2371621A describe detecting gas compounds by combining infrared spectrophotometry and a membrane separation process. US20060008913 A1 describes the use of a perfluoro-based polymer for oil-water separation in microfluidic system.

SUMMARY OF THE INVENTION

In accordance with an embodiment of the invention, apparatus for performing in situ analysis of borehole fluid includes a gas separation system and a gas detection system. The gas separation system may include a membrane. The gas separated from the fluid by the membrane may be detected by techniques such as reaction with another material or spectroscopy. When spectroscopy is employed, a test chamber is used to hold the gas undergoing test. Various techniques may be employed to protect the gas separation system from damage due to pressure differential. For example, a separation membrane may be integrated with layers that provide strength and rigidity. The integrated separation membrane may include one or more of a water impermeable layer, gas selective layer, inorganic base layer and metal support layer. The gas selective layer itself can also function as a water impermeable layer. The metal support layer enhances resistance to differential pressure. Alternatively, the test chamber may be filled with a liquid or solid material.

In accordance with another embodiment of the invention, a method for downhole fluid analysis comprises: sampling a downhole fluid; taking a gas from the downhole fluid by using a gas separation module; and sensing the gas.

One of the advantages of the invention is that borehole fluid can be analyzed in situ. In particular, gas is separated from the fluid and detected within the borehole. Consequently, time consuming fluid retrieval and errors caused by changes to fluid samples due to changes in conditions between the borehole and the environment are at least mitigated.

DETAILED DESCRIPTION

Figure 1:
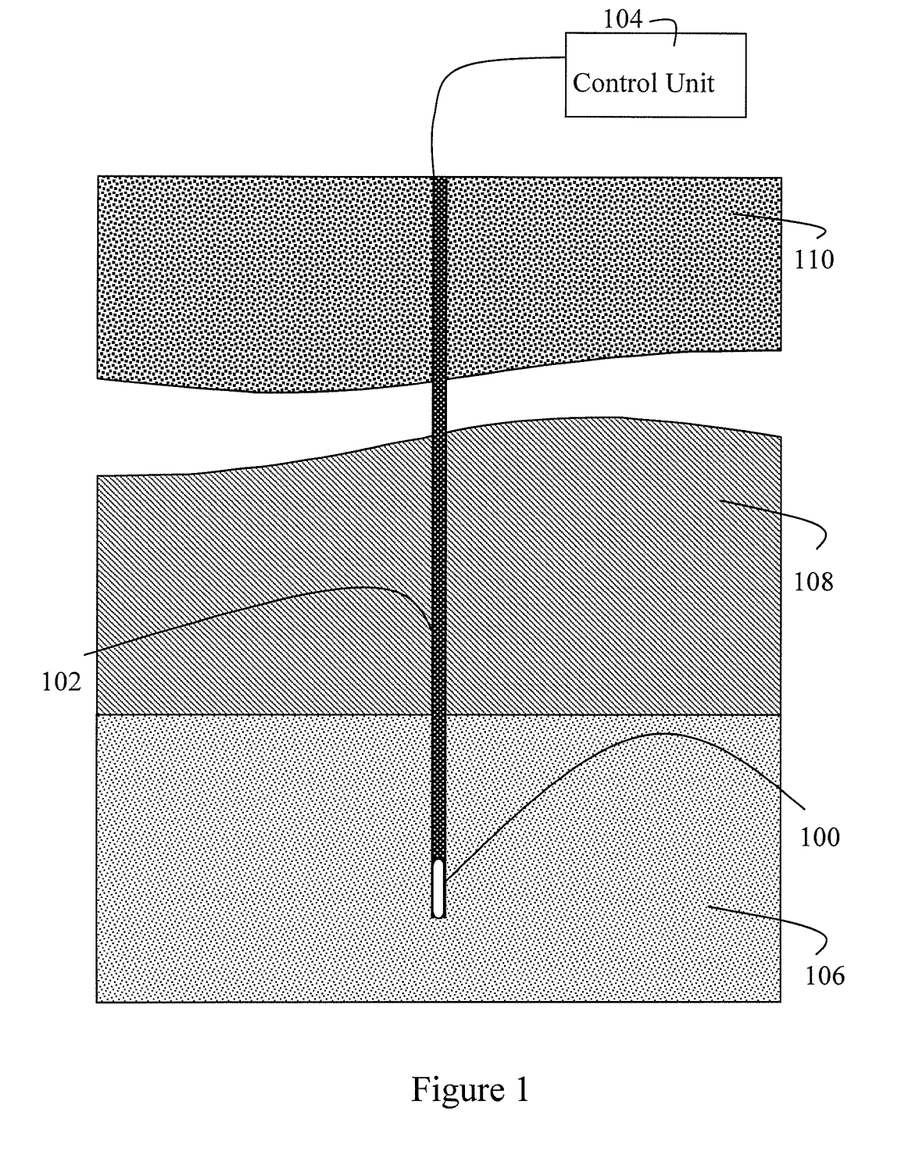
FIG. 1 illustrates a logging tool for gas separation and detection in a borehole.

Referring to FIG. 1, a wireline logging tool (106) is suspended from an armored cable (108), and may have optional centralizers (not shown). The cable (108) extends from the borehole (104) over a sheave wheel (110) on a derrick (112) to a winch forming part of surface equipment, which may include an analyzer unit (114). Well known depth gauging equipment (not shown) may be provided to measure cable displacement over the sheave wheel (110). The tool (106) may include any of many well known devices to produce a signal indicating tool orientation. Processing and interface circuitry within the tool (106) amplifies samples and digitizes the tool's information signals for transmission and communicates them to the analyzer unit (114) via the cable (108). Electrical power and control signals for coordinating operation of the tool (106) may be generated by the analyzer unit (114) or some other device, and communicated via the cable (108) to circuitry provided within the tool (106). The surface equipment includes a processor subsystem (116) (which may include a microprocessor, memory, clock and timing, and input/output functions—not separately shown), standard peripheral equipment (not separately shown), and a recorder (118). The logging tool (106) is representative of any logging device that may be used in accordance with principles described herein. It will be understood by those of skill in the art having the benefit of this disclosure that the gas separation and detection tool described in detail below can be implemented as a wireline, MWD, LWD, or other type of tool, including but not limited to tools mounted in the formation or mounted in a completion of the borehole to perform ongoing measurements over time.

Figure 2:
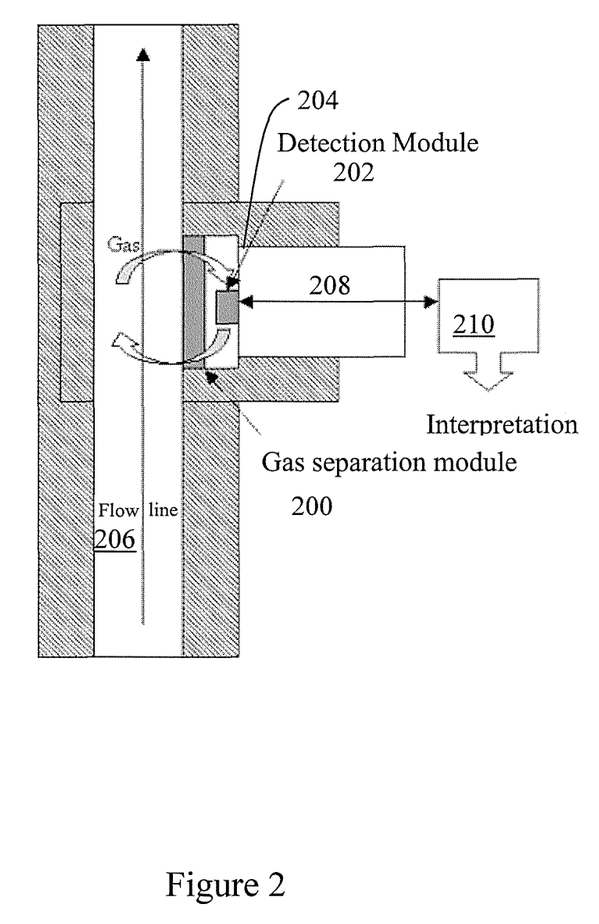
FIG. 2 illustrates an embodiment of the tool for gas separation and detection in greater detail.

Referring to FIG. 2, an embodiment of the gas separation and detection tool includes a separation module (200) and a detection module (202). A test chamber (204) may also be defined between the separation module and detection module. Gas that is present in a borehole fluid in a flowline (206) enters the chamber via the separation module, i.e., the gas is separated from the fluid in the flowline. Differential pressure between the flow line and the chamber may facilitate gas separation. The detection module subjects the separated gas in the chamber to a testing regime which results in production of an indicator signal (208). The indicator signal is provided to interpretation circuitry (210) which characterizes the gas sample, e.g., in terms of type and concentration.

Figure 3:
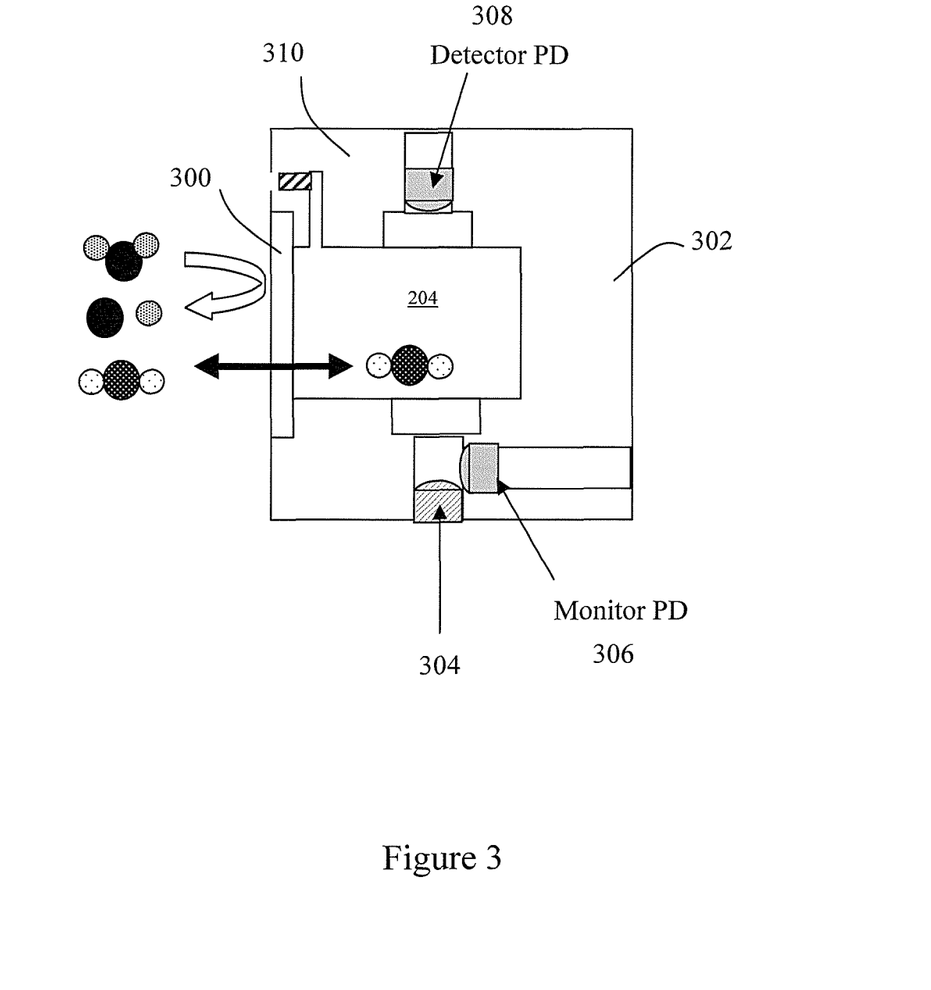
FIG. 3 illustrates an embodiment of the gas separation and detection tool of FIG. 2 having a gas separation membrane and spectroscopy sensor.

Referring to FIGS. 2 and 3, the separation module may include a membrane (300). The membrane has characteristics that inhibit traversal by all but one or more selected compounds. One embodiment of the membrane (300) is an inorganic, gas-selective, molecular separation membrane having alumina as its base structure, e.g., a DDR type zeolite membrane. Nanoporous zeolite material is grown on the top of the base material. Examples of such membranes are described in US20050229779A1, US6953493B2 and US20040173094A1. The membrane has a pore size of about 0.3-0.7 nm, resulting in a strong affinity towards specific gas compounds such as CO2. Further enhancement of separation and selectivity characteristics of the membrane can be accomplished by modifying the surface structure. For example, a water-impermeable layer such as a perfluoro-based polymer (e.g. Teflon AF or its variations), polydimethyl siloxane based polymer, polyimide-based polymer, polysulfone-based polymer or polyester-based polymer may be applied to inhibit water permeation through the membrane. Other variations of the separation membrane operate as either molecular sieves or adsoption-phase separation. These variations can formed of inorganic compounds, inorganic sol-gel, inorganic-organic hybrid compounds, inorganic base material with organic base compound impregnated inside the matrix, and any organic materials that satisfy requirements.

The chamber (204), if present, is defined by a rigid housing (302). The membrane (300) occupies an opening formed in the housing (302). The housing and membrane isolate the chamber from the fluid in the flowline, except with respect to compounds that can traverse the membrane. As already mentioned, when partial pressure of gas compounds is greater in the flowline than in the chamber, differential pressure drives gas from the flowline into the chamber. When the partial pressure is greater in the chamber than in the flowline, differential pressure drives gas from the chamber into the flowline. In this manner the chamber can be cleared in preparation for subsequent tests.

Operation of the detector module (202) may be based on techniques including but not limited to infrared (IR) absorption spectroscopy. An IR absorption detector module may include an infrared (IR) light source (304), a monitor photodetector (PD) (306), an IR detector (308), and an optical filter (310). The IR source (304) is disposed relative to the optical filter (310) and IR detector (308) such that light from the IR source that traverses the chamber (204), then traverses the filter (unless filtered), and then reaches the IR detector. The module may be tuned to the 4.3 micrometer wavelength region, or some other suitable wavelength. The monitor PD (306) detects the light source power directly, i.e., without first traversing the chamber, for temperature calibration. If multiwavelength spectroscopy is used, e.g., for multi-gas detection or baseline measurement, several LEDs or LDs can be provided as light sources and a modulation technique can be employed to discriminate between detector signals corresponding to the different wavelengths. Further, spectroscopy with NIR and MIR wavelengths may alternatively be employed. In each of these variant embodiments the absorbed wavelength is used to identify the gas and the absorption coefficient is used to estimate gas concentration.

Figure 4:
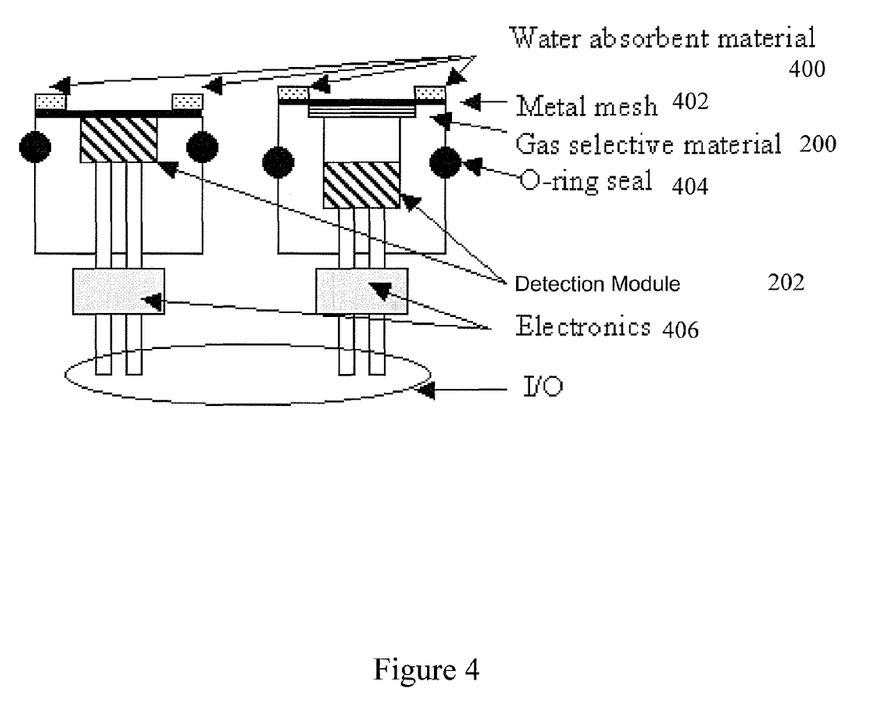
FIG. 4 illustrates alternative embodiments of the gas separation and detection tool, both with and without sampling chamber.

FIG. 4 illustrates embodiments of the invention both with and without a test chamber. These embodiments may operate on the principle of measuring electromotive force generated when the gas reacts with a detecting compound, i.e., the gas sensor module (202) includes a compound that reacts with the target gas. Because the electromotive force resulting from the reaction is proportional to the gas concentration, i.e., gas partial pressure inside the system, gas concentration in the flowline can be estimated from the measured electromotive force. Alternatively, these embodiments may operate on the principle of measuring resistivity change when the gas reacts with the detecting compound. Because the resistivity change is proportional to the gas concentration, i.e., gas partial pressure inside the system, gas concentration in the flowline can be estimated from the measured resistivity change.

Other features which enhance operation may also be utilized. For example, a water absorbent material (400) may be provided to absorb water vapor that might be produced from either permeation through the membrane or as a by product of the reaction of the gas with a detecting compound. Examples of water absorbant material include, but are not limited to, hygroscopic materials (silica gel, calcium sulfate, calcium chloride, montmorillonite clay, and molecular sieves), sulfonated aromatic hydrocarbons and Nafion composites. Another such feature is a metal mesh (402) which functions as a flame trap to help mitigate damage that might be caused when gas concentration changes greatly over a short span of time. Another such feature is an O-ring seal (404) disposed between the housing and the flowline to help protect detection and interpretation electronics (406). Materials suitable for construction of components of the gas sensor module include $SnO_2$, doped with copper or tungsten, gold epoxy, gold, conductive and non-conductive polymer, glass, carbon compounds and carbon nanotube compounds for the purpose of proper sealing, maintaining good electrical connection, increasing sensitivity and obtaining stable measurements. The housing may be made of high performance thermoplastics, PEEK, Glass-PEEK, or metal alloys (Ni).

Figure 5:
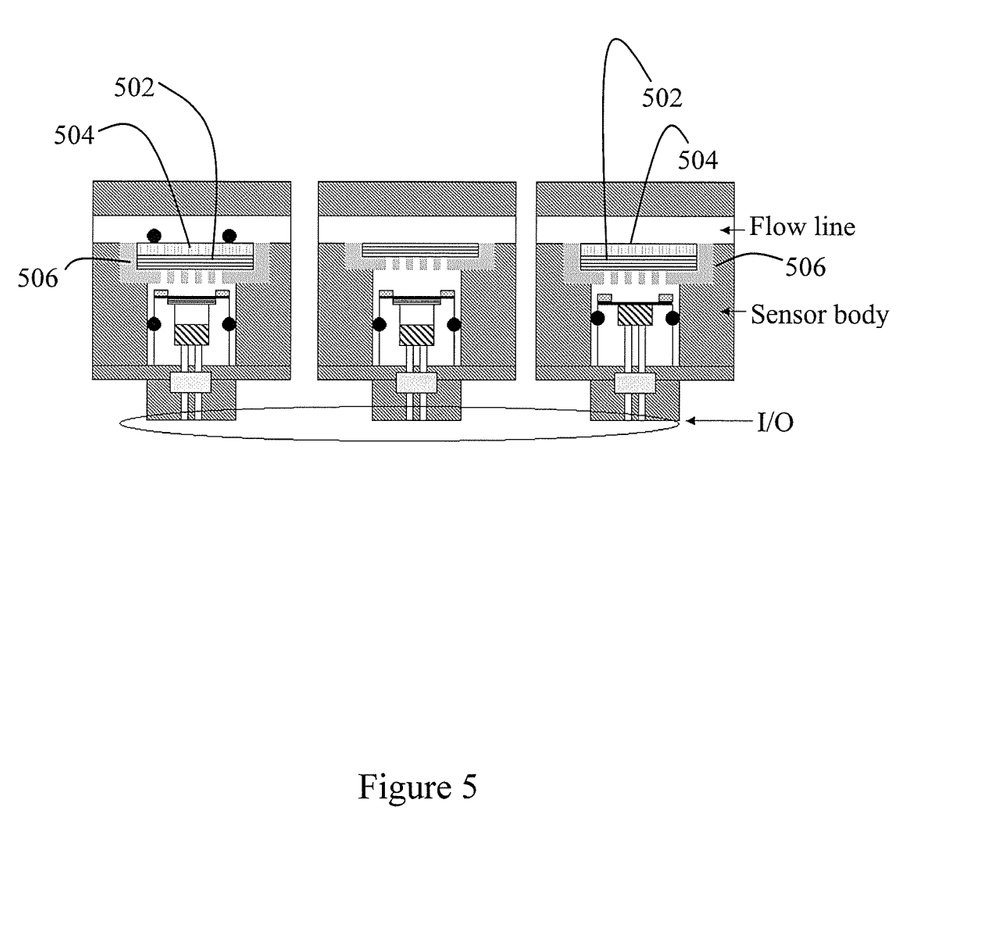
FIG. 5 illustrates embodiments of the gas separation and detection tool with different integrated membranes.
Figure 6:
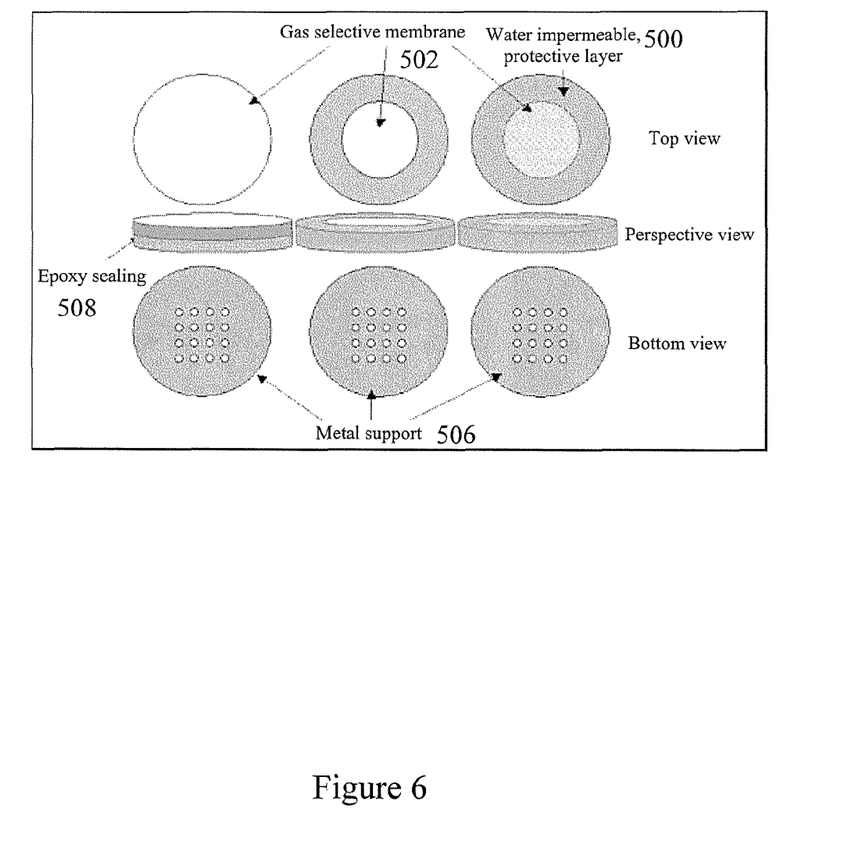
FIG. 6 illustrates embodiments of the integrated membrane in greater detail.

Referring to FIGS. 5 and 6, various features may be employed to help protect the membrane from damage, e.g., due to the force caused by the pressure differential where the chamber contains only gas. One such feature is an integrated molecular separation membrane. The integrated membrane can include a water impermeable protective layer (500), a gas selective membrane (502), an inorganic base layer (504) and a metal support layer (506). The metal support layer increases the mechanical strength of the membrane at high-pressure differentials. Gas permeates through the molecular separation layer and goes into the system via small holes in the metal support. In another embodiment the integrated molecular separation membrane includes a molecular separation membrane/layer bonded to a metal support layer and sealed with epoxy (508) or any other sealant. The epoxy can be a high temperature-resistant, non-conductive type of epoxy or other polymeric substances. The molecular separation layer can act as a water/oil separation membrane. Gas permeates through the molecular separation layer and goes into the system via small holes in the metal support. In another embodiment the integrated separation membrane includes a molecular separation membrane/layer bonded to a metal support layer and sealed with epoxy (508). The metal support is designed to accommodate insertion of the molecular separation membrane. The epoxy or sealant can be a high temperature, non-conductive type of epoxy or other polymeric substances. Gas permeates through the molecular separation layer and goes into the system via small holes in the metal support.

Figure 7:
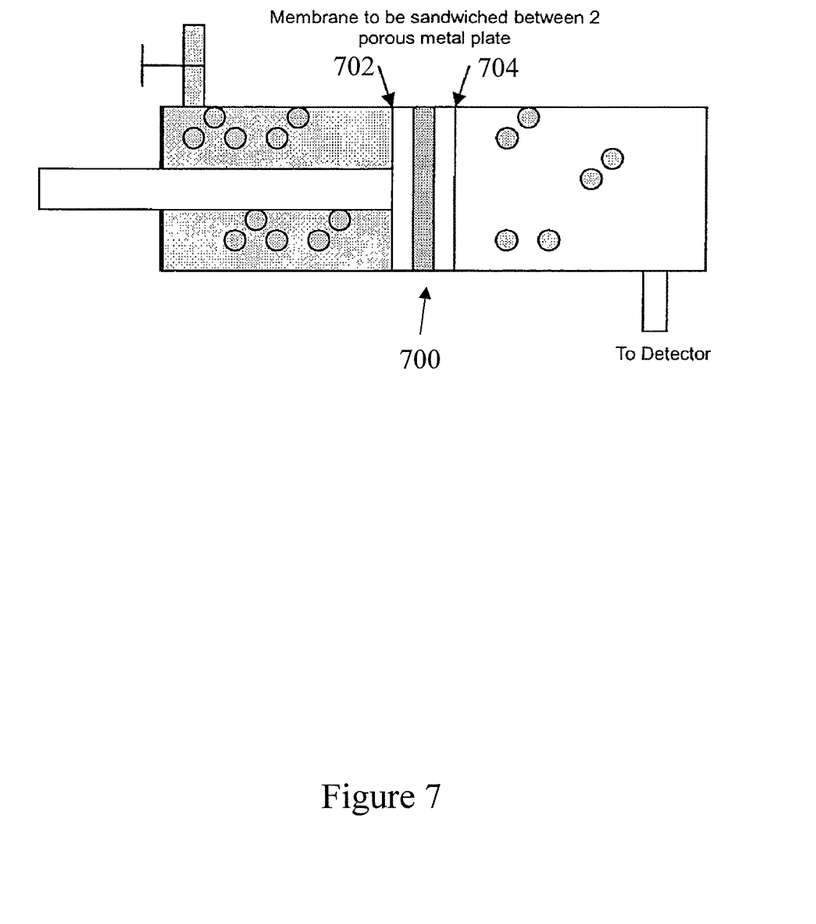
FIG. 7 illustrates another alternative embodiment of the gas separation and detection tool with an integrated membrane.

Referring to FIG. 7, in an alternative embodiment the integrated membrane includes a molecular separation membrane/layer (700) bonded between porous metal plates (702, 704). In addition to integrating the gas separation and pressure balancing functions into one mechanical assembly, this alternative embodiment provides support for the membrane both at a pressure differential where flowline pressure is greater than chamber pressure and at a pressure differential where chamber pressure is greater than flowline pressure.

Figure 8:
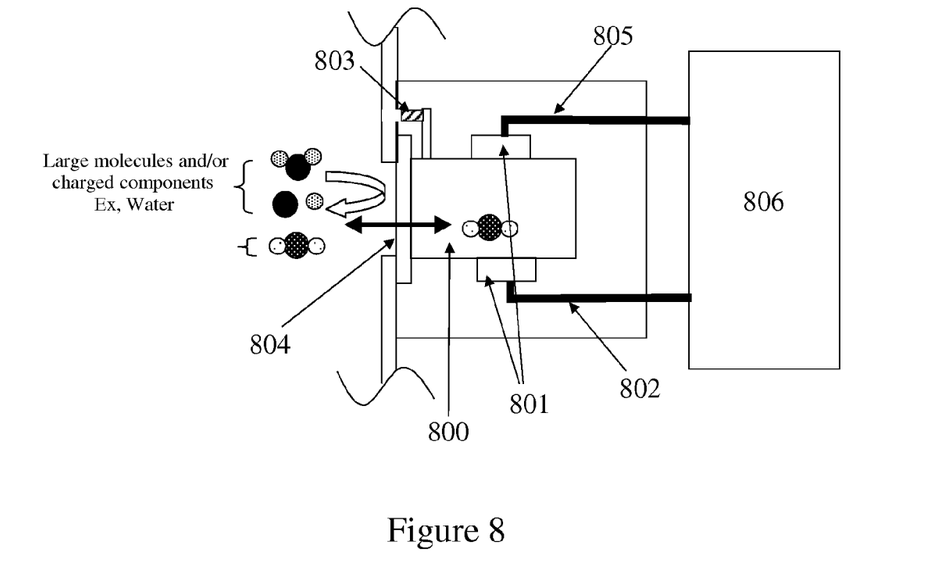
FIG. 8 illustrates an embodiment of the gas separation and detection tool with a fluidic buffer.

Referring to FIG. 8, an alternative embodiment utilizes an incompressible liquid buffer (800) to help prevent membrane damage due to pressure differential. The liquid buffer (800) may be implemented with a liquid material that does not absorb the target gas. Because the liquid buffer is incompressible, buckling of the membrane due to the force caused by higher pressure in the flowline than in the chamber is inhibited when the chamber is filled with liquid buffer. A bellows (803) can be provided to compensate for small changes in compressibility within the chamber due to, for example, introduction or discharge of the target gas. The bellow is one example of a pressure compensator. FIG. 8 illustrates a membrane (804) and a spectrometer module (806), to which the above embodiments of FIGS. 2-7 can be applied either alone or in combination. FIG. 8 illustrates an optical window (801), an input optical path (802) and an output optical path (805).

Figure 9:
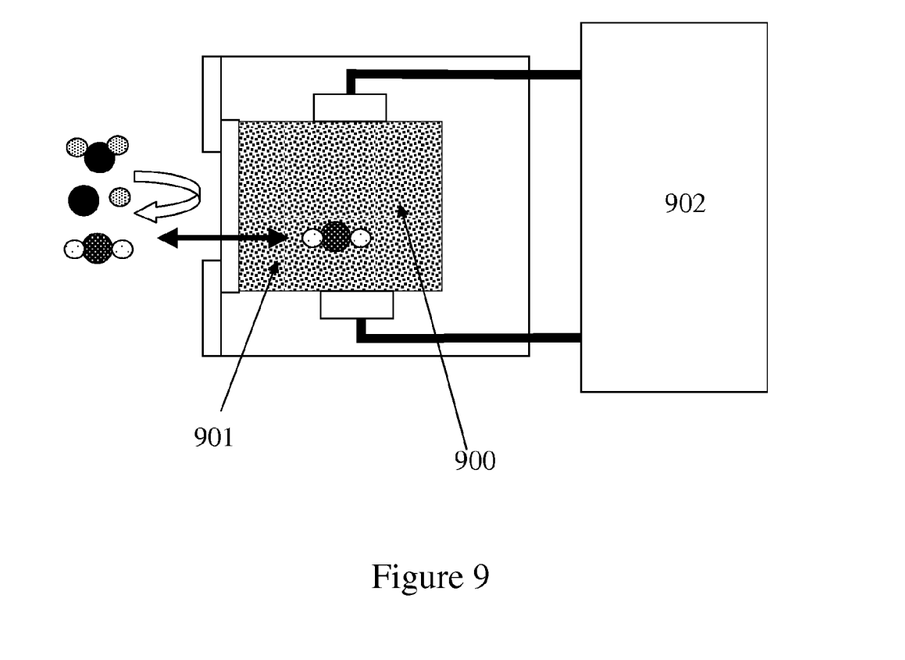
FIG. 9 illustrates a solid state embodiment of the gas separation and detection tool.

FIG. 9 illustrates an alternative embodiment that is different from the above embodiments of FIGS. 2-7 in utilizing a solid state chamber (900). The solid state chamber is formed by filling the cavity defined by the housing with a nanoporous solid material (901). Suitable materials include, but are not limited to, $TiO_2$, which is transparent in the NIR and MIR range. The target gas which traverses the membrane enters the nanospace of the solid material. Since the chamber is solid state, buckling of the membrane due to higher pressure in the flowline than in the chamber is inhibited. However, because the chamber is porous, gas can be accommodated. FIG. 9 illustrates a spectrometer module (902).

FIG. 9 illustrates an alternative embodiment that is different from the above embodiments of FIGS. 2-7 in utilizing a solid state chamber (900). The solid state chamber is formed by filling the cavity defined by the housing with a nanoporous solid material. Suitable materials include, but are not limited to, $TiO_2$, which is transparent in the NIR and MIR range. The target gas which traverses the membrane enters the nanospace of the solid material. Since the chamber is solid state, buckling of the membrane due to higher pressure in the flowline than in the chamber is inhibited. However, because the chamber is porous, gas can be accommodated.

Figure 10:
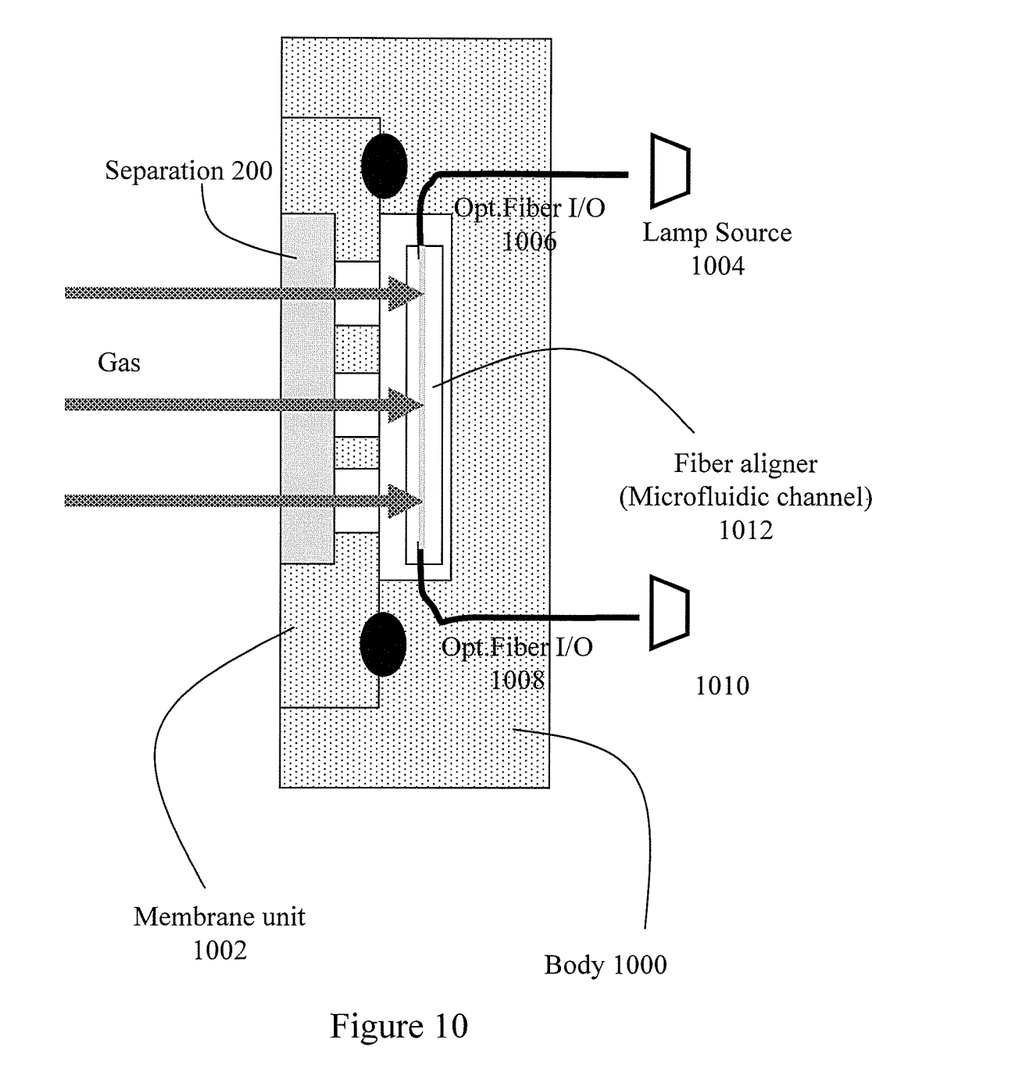
FIG. 10 illustrates an alternative embodiment of the gas separation and detection tool.

FIG. 10 illustrates another alternative embodiment of the gas separation and detection tool. The tool includes a non H2S-scavenging body (1000) with a gas separation module (200) which may include a membrane unit (1002) as illustrated in FIGS. 2-9. The separated gas enters a test chamber defined by the body and membrane unit due to differential pressure. A monochromator including optical fibre is used to facilitate gas detection. In particular, light from a lamp source (1004) is inputted to an optical fibre (1006), which is routed to one side of the chamber. A corresponding optical fibre (1008) is routed to the opposite side of the chamber, and transports received light to a receiver (1010). A microfluidic channel fibre alignment feature (1012) maintains alignment between the corresponding fibres (1006, 1008). The arrangement may be utilized for any of various gas detection techniques based on spectroscopy, including but not limited to infrared (IR) absorption spectroscopy, NIR and MIR. In each of these variant embodiments the absorbed wavelength is used to identify the gas and the absorption coefficient is used to estimate gas concentration.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. An apparatus for downhole fluid analysis, comprising:
    a sampling chamber for a downhole fluid, wherein the sample chamber comprises a detector module with an opening;
    a gas separation module for taking a gas from the downhole fluid, wherein the gas separation module comprises a membrane located in the opening, a support for holding the membrane, and a sealant applied between the membrane and the support; and
    a gas detector for sensing the gas.

2. The apparatus of claim 1, wherein the gas separation module is provided for the opening.

3. The apparatus of claim 1, wherein the sampling chamber further comprises a flowline, wherein the gas separation module is provided between the flowline and the detector cell.

4. The apparatus of claim 1, wherein the membrane comprises a DDR type zeolite.

5. The apparatus of claim 1, wherein the membrane comprises at least one selectively permeable layer and at least one selectively impermeable layer, such that the at least one selectively permeable layer allows one portion of the downhole fluid to pass through, and the at least one selectively impermeable layer prevents another portion of the downhole fluid from passing through the at least one selectively permeable layer.

6. The apparatus of claim 1, wherein the support is located on the membrane.

7. The apparatus of claim 1, wherein the gas comprises a carbon dioxide, a hydrogen sulfide, and/or a methane.

8. The apparatus of claim 1, wherein the gas detector comprises an infrared light source and an infrared light transducer.

9. The apparatus of claim 8, wherein the gas detector further comprises a monochromator disposed between the infrared light source and the infrared light transducer.

10. The apparatus of claim 8, wherein the detector module comprises an optical window so that the infrared light source transmits an infrared light to the detector module chamber through the optical window.

11. The apparatus of claim 1, wherein the detector module comprises a pressure compensator.

12. The apparatus of claim 11, wherein the pressure compensator is a bellows provided between the gas separation module and the detector module.

13. The apparatus of claim 11, wherein the pressure compensator comprises a buffer material which occupies an internal space of the detector module independently of the gas detector.

14. The apparatus of claim 13, wherein the buffer material comprises a liquid material.

15. The apparatus of claim 13, wherein the buffer material comprises a solid material.

16. The apparatus of claim 15, wherein the solid material is porous.

17. The apparatus of claim 15, wherein the solid material comprises a titanium dioxide.

18. A method for downhole fluid analysis, comprising:
sampling a downhole fluid in a sampling chamber comprising a detector module with an opening;
taking a gas from the downhole fluid by using a gas separation module, wherein the gas separation module comprises a membrane located in the opening, a support for holding the membrane, and a temperature-resistant and non-conductive sealant applied between the membrane and the support; and
sensing the gas.

* * * * *